United States Patent
Fiorini-Puybaret

(10) Patent No.: US 10,925,915 B2
(45) Date of Patent: Feb. 23, 2021

(54) **USE OF A *COPAIFERA* EXTRACT TO COMBAT ALOPECIA AND SEBORRHEA**

(71) Applicant: PIERRE FABRE DERMO-COSMETIQUE, Boulogne-Billancourt (FR)

(72) Inventor: Christel Fiorini-Puybaret, Toulouse (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 0 days.

(21) Appl. No.: 16/495,764

(22) PCT Filed: Mar. 20, 2018

(86) PCT No.: PCT/EP2018/057075
§ 371 (c)(1),
(2) Date: Sep. 19, 2019

(87) PCT Pub. No.: WO2018/172379
PCT Pub. Date: Sep. 27, 2018

(65) Prior Publication Data
US 2020/0108111 A1    Apr. 9, 2020

(30) Foreign Application Priority Data

Mar. 20, 2017 (FR) ..................... 1752281

(51) Int. Cl.
*A61K 36/00* (2006.01)
*A61K 36/48* (2006.01)
*A61P 17/14* (2006.01)

(52) U.S. Cl.
CPC .............. *A61K 36/48* (2013.01); *A61P 17/14* (2018.01)

(58) Field of Classification Search
CPC ....................................... A61K 3/00

USPC ......................................... 424/725
See application file for complete search history.

(56) References Cited

FOREIGN PATENT DOCUMENTS

| FR | 2 816 843 A1 | 5/2002 |
| KR | 10-0863616 B1 | 10/2008 |
| WO | WO 2013/084163 A1 | 6/2013 |

OTHER PUBLICATIONS

Author Unknown, "Prima Fleur Recommends Treating Skin to Nourishing Vegetable Oil and Essential Oil Serums to Target Any Skin Condition", Massage Magazine, URL: https://www.massagemag.com/, Jul. 27, 2011, 3 pages.
Database WPI Week 200923, Thomson Scientific, London, GB, AN 2009-E69339, XP002776851, 2 pages.
Database WPI Week 201707, Thomson Scientific, London, GB, AN: 2016-72170C, XP002776855 (2 pages total).
Gomes Da Silva et al., "Application of the Essential Oil from Copaiba (*Copaifera langsdorffii* Desf.) for Acne Vulgaris: a Double-Blind, Placebo Controlled Clinical Trial", Alternative Medicine Review, vol. 17, No. 1, 2012, pp. 69-75.
International Search Report dated Jun. 12, 2018, for International Application No. PCT/EP2018/057075.
Leandro et al., "Chemistry and Biological Activities of Terpenoids from Copaiba (*Copaifera* spp.) Oleoresins", Molecules, vol. 17, Mar. 30, 2012, pp. 3866-3889.
Veiga et al., "Phytochemical and antioedematogenic studies of Commercial Copaiba Oils Available in Brazil", Phytotherapy Research, vol. 15, No. 6, 2001, pp. 476-480.
Whiting et al., "Measuring Reversal of Hair Miniaturization in Androgenetic Alopecia by Follicular Counts in Horizontal Sections of Serial Scalp Biopsies: Results of Finasteride 1 mg Treatment of Men and Postmenopausal Women", JID Symposium Proceedings, vol. 4, No. 3, Dec. 1999, pp. 287-284.

*Primary Examiner* — Michael V Meller
(74) *Attorney, Agent, or Firm* — Birch, Stewart, Kolasch & Birch, LLP

(57) ABSTRACT

The present invention relates to the cosmetic and dermatological use of a *Copaifera* extract in the treatment and/or prevention of alopecia and in the treatment of seborrhea.

17 Claims, No Drawings

USE OF A *COPAIFERA* EXTRACT TO COMBAT ALOPECIA AND SEBORRHEA

The present invention relates to the use of an extract of *Copaifera* in cosmetics and dermatology in the treatment and/or prevention of alopecia as well as in the treatment of seborrhoea.

PRIOR ART

The genus *Copaifera* includes 35 species, all of which are trees from tropical America, i.e. Mexico, northern Argentina and mainly Brazil. On the territory there are more than twenty species, the most abundant being *C. officinalis, C. reticulta, C. multijuga. Copaifeira officinalis* is a tree found mainly in Brazil, Colombia and Venezuela. It has reddish-brown wood and grows to 25 m. The leaves are composed, paripinnate with 2 to 10 leaflets, alternate or sub-opposite, apiculate and unevenly rounded at the base. They are 3-8 cm long and 2-4 cm wide. The white flowers, generally sessile, are grouped into inflorescences of 7-14 cm. The fruits are small pods swollen at maturity with a diameter of 20-25 mm, glabrous, apiculate containing an ovoid seed.

Oleoresin is a substance obtained by incising the bark of several *Copaifera* species. Located in anastomosed secretory channels of the secondary wood and the marrow, its extraction therefore requires very deep incisions of the trunk which allows it to flow naturally from the tree.

After steam distillation or hydrodistillation, the oleoresin makes it possible to obtain Copaiba essential oil, famous in perfumery.

Copaiba oleoresin has been used in medicine since the 16th century by the indigenous people of Brazil. It has a long history of use in traditional Brazilian medicine, to treat wounds and remove scars, as febrifuge, urinary tract antiseptic, against leucorrhoea and gonorrhoea. Considered a general tonic, its indications were as follows: venereal disease, respiratory disease, asthma, rheumatism, secondary skin lesions, ulcers. At low doses, it is a stimulant with direct action on the stomach. Copaiba oleoresin reduces excessive mucus secretion caused by inflammation. Today, Copaiba oleoresin is sold in capsules in pharmacies in Brazil where it is indicated for all types of internal inflammation and stomach ulcers. When applied locally, it is a powerful antiseptic and anti-inflammatory healing agent, it helps to heal the most difficult wounds. Copaiba oleoresin is said to be very effective on joint pain, benign sprains, hematomas, tendonitis. Oleoresin is applied directly to the skin. Oleoresin is also used as a massage oil for painful or inflamed muscles and joints.

*Copaifera* oleoresin, optionally distilled, is also used in cosmetics, in the manufacture of soaps, bubble baths, detergents and creams, and as a fixative in perfumery. Oleoresin is sometimes used as a flavouring agent in the food industry. Copaiba oleoresin is also used as material for artists, particularly in oil paint recipes and in decorative ceramics.

Oleoresin is a colourless and thin liquid which acquires an oleaginous consistency and a greenish-yellow colour over time. Its consistency and colour vary slightly, depending on the tree from which it comes and on the essential oil found there. Its smell is strong and unpleasant, its flavour is bitter and pungent. Oleoresin is insoluble in water, totally soluble in alcohol and in ether.

The oleoresin of *Copaifera officinalis* consists of two fractions which are distinguished by their volatility; each of the fractions being characterized by distinct chemical compounds:

A "volatile" essential oil representing 50-90% of the oleoresin, which is mainly composed of sesquiterpenes. Among these sesquiterpenes, mainly germacrene D, (E)-β-caryophyllene, β- and δ-elemene, α-ylangene, α-gurjunene, α-humulene can be distinguished. The minority sesquiterpenes are α-cubebene, α-copaene, 7-epi-sesquithujene, cis- and trans-α-bergamotene, sesquisabinene-A and -B, 4αH,10αH-guaia-1(5),6-diene, allo-aromadendrene, γ-uurolene, α-amorphene, β-selinene, bicycliosesquiphyllandrene, α-muurolene, β-bisabolene, γ-cadinene, δ-cadinene, cis-calamene, zonarene, cakina-1'4-diene, α-cadinene, α-calacorene, selina-3,7(11)-diene, germacrene B. This volatile oil is very clear, colourless, with a very pronounced smell and taste.

A "non-volatile" fraction representing 10-50% of the oleoresin, which is composed mainly of the following diterpenic acids and/or diterpenic acid esters: copalic acid, copaiferolic acid, agathendioic acid dimethyl ester, agathic acid, 3β-hydroxyanticopalic acid methyl ester, hardwickiic acid, 7α-acetoxyhardwickiic acid. This distillation residue is a viscous liquid with an aromatic odour and a dark brown colour.

KR10-0863616 describes various cosmetic and therapeutic uses of the volatile fraction of *Copaifera* oleoresin, i.e. the essential oil. This document teaches that this essential oil has many anti-wrinkle, anti-inflammatory, hair growth-stimulating, anti-obesity, antioxidant, immunosuppressive and skin-whitening properties. With regard to the anti-alopecia properties claimed in this document for this essential oil, it is applied topically to the scalp of bald patients and the effect on hair follicle regeneration is found to be equivalent to that observed with minoxidil. However, no effect on preventing hair loss has been demonstrated.

Gomes da Silva et al. (Alternative Medicine Review; 17; 1; p 69-75) describe the anti-acne effect of *Copaifera* essential oil. In its introduction, this article confirms that the oleoresin known for its many anti-inflammatory, antiseptic and healing properties is composed of two fractions, a sesquiterpenic (contained in the volatile essential oil) and a diterpenic (contained in the non-volatile fraction). In the tests performed by Gomes da Silva et al., the essential oil (i.e. sesquiterpene-rich volatile fraction) is applied to volunteers with type 1 acne (non-inflamed comedones). The conclusion of these tests is that the essential oil containing the volatile sesquiterpenic fraction of Copaiba oleoresin could be useful in the treatment of mild acne and the authors suggest a potential role in inhibiting the growth of *Propionibacterium* acnes in the anti-acne effect of this essential oil.

Many studies have therefore focused on the volatile fraction of *Copaifera* oleoresin with regard to its therapeutic properties.

SUMMARY OF THE INVENTION

The inventors have shown that, quite surprisingly, *Copaifera* oleoresin, via its non-volatile fraction, has particularly advantageous and beneficial dermatological and cosmetic properties by virtue of its inhibitory effect on the enzyme 5α-reductase.

This property is relevant for uses in cosmetics and dermatology in the treatment or prevention of alopecia as well as in the treatment of seborrhoea.

DETAILED DESCRIPTION

Alopecia is defined as partial or total hair loss. The life of a hair follows a cycle, called the hair cycle, during which three phases follow in succession. The anagen phase is a period of active and continuous growth associated with intense metabolic activity in the bulb. The catagen phase is characterized by a slowing of mitotic activity. The hair undergoes involution, the follicle atrophies and its dermal implantation appears to rise. The last phase is the telogen phase during which the follicle rests and the hair is eventually pushed out by a new hair. The hair cycle is complete, another one can begin. In humans, the life of each bulb goes through about 20 to 25 cycles. As we age, our hair becomes thinner and its cycles shorter.

Androgenetic alopecia is due to an acceleration of the hair cycle (shortening of the duration of the hair cycle), a phenomenon that first leads to the appearance of miniaturized hair called "vellus" hair and then to a premature exhaustion of hair renewal. Indeed, the duration of the anagen phase (growth phase) is shortened from several years (2 to 5 years) to a few months or even a few weeks (Whiting et al., J Investig Dermatol Symp Proc, 1999). The consequence is early hair loss.

It is known to date that the mechanisms responsible for hereditary androgenetic alopecia (formerly known as seborrhoeic alopecia) involve, among other things, the hormonal component with overexpression of the androgen receptor (testosterone and DHT receptor) and more intense 5α-reductase activity. This hormonal deregulation leads to excessive production of dihydrotestosterone, the active metabolite of testosterone. In the dermal papilla, this metabolite will stimulate the production of hair cycle inhibitors, leading to a shortening of the anagen phase, forcing the hair to switch too quickly to the telogen phase and leaving the hair follicle insufficient time to produce a quality keratin and necessarily after several cycles, an exhaustion of the hair follicle's ability to produce a hair shaft.

This excess androgen-related alopecia also affects women at menopause (post-menopausal alopecia) or following treatment with androgens. It begins at the temples and at the crown. This hair loss is more diffuse and widespread than in men. Hair loss affects the entire scalp homogeneously.

An active ingredient that inhibits 5α-reductase could thus be used to treat and/or prevent hair loss in men and/or women.

As for seborrhoea, it corresponds to an excessive production of sebum by the sebaceous glands. On the whole, man has 2,000,000 sebaceous glands attached to 6,000,000 hairs of the head and body. The distribution of sebaceous glands is not uniform. The density of the sebaceous glands reaches 300 to 900 sebaceous glands/cm$^2$ on the face and scalp and about 100 sebaceous glands/cm$^2$ on the upper chest and back.

The activity of the sebaceous gland is influenced by androgens. Androgens are only active under the influence of 5α-reductase which ensures the metabolization of androgens in the sebaceous gland, which induces sebum production. Hyperactivation of 5α-reductase causes seborrhoea.

The site of seborrhoea manifestations is the midfacial region (forehead, nose, chin) where the sebaceous glands are the most numerous and the most voluminous. Seborrhoea also occurs in the scalp where it predominates in the frontal and frontotemporal regions and at the top of the skull.

Seborrhoea causes aesthetic and dermatological problems such as seborrhoeic dermatitis. As for the skin, it has a shiny appearance, the complexion is dull and the pilosebaceous orifices are dilated. Moreover, make-up does not hold well on this type of oily skin.

For seborrhoea of the scalp, the hair looks oily and dull and is difficult to style. When seborrhoea is intense, it is called oily, fluent and can be associated with a rancid smell. Seborrhoea is often associated with androgenetic alopecia.

An active inhibitor of 5α-reductase activity thus makes it possible to reduce sebum secretion, treat seborrhoea and resolve the aesthetic problems associated with seborrhoea.

Thus, the present invention concerns, in a first embodiment, an extract of *Copaifera* comprising or consisting of, as 5α-reductase inhibitor active principle, a mixture of diterpenic acids and/or diterpenic acid esters, for use in the prevention and/or treatment of dermatological conditions selected from seborrhoea and alopecia. Preferably, it is the treatment of alopecia.

In a second embodiment of the invention, the *Copaifera* is selected from the following plant species: *Copaifera officinalis, Copaifera multijuga* and *Copaifera reticulata*; used alone or in mixture.

The *Copaifera* extract comprising a mixture of diterpenic acids and/or diterpenic acid esters according to the invention may be a refined *Copaifera* plant extract and containing, by weight based on the total weight of the extract, between 7.5 and 95 wt % diterpenic acids and/or diterpenic acid esters.

The *Copaifera* extract according to the invention advantageously comprises, or consists of, a *Copaifera* oleoresin containing at least 7.5 wt % of a mixture of diterpenic acids and/or diterpenic acid esters, particularly at least 15 wt %, more particularly at least 20 wt %, more particularly still at least 25 wt %; based on the total weight of the *Copaifera* oleoresin. The *Copaifera* extract according to the invention may comprise, or consist of, a *Copaifera* oleoresin enriched in a mixture of diterpenic acids and/or diterpenic acid esters containing, in weight percentage, between 48 and 90 wt % diterpenic acids and/or diterpenic acid esters, more particularly between 50 and 90 wt %, more particularly between 60 and 90 wt %, more particularly between 70 and 90 wt %, more particularly between 80 and 90 wt %; based on the total weight of the enriched *Copaifera* oleoresin.

The invention also relates to a *Copaifera* extract according to the invention for use as an anti-seborrhoea active principle in a dermatological composition for treating and/or preventing seborrhoea, characterized in that said extract is the only anti-seborrhoea active principle in said composition.

The invention also relates to a *Copaifera* extract according to the invention for use as an anti-alopecia active principle in a dermatological composition for treating and/or preventing alopecia, characterized in that said extract is the only anti-alopecia active principle in said composition.

For the purposes of the present invention, the term "enriched" means that the oleoresin in the extract has an increased concentration of diterpenic acids and/or diterpenic acid esters compared with the native oleoresin—i.e. obtained directly from the tree—by various processes for increasing this concentration in said diterpenic acids and/or diterpenic acid esters; this increase in concentration being preferentially for said acids and esters compared with the other oleoresin compounds, which are only slightly concentrated if at all. Enrichment can be achieved by treatment via a process to concentrate the content of these 7 diterpenic acids and/or diterpenic acid esters with respect to other compounds and molecules. Such enrichment mainly includes the at least partial removal of the volatile fraction (i.e. essential oil).

The mixture of diterpenic acids and/or diterpenic acid esters comprises at least 2, or at least 3, or at least 4, or at least 5, or at least 6, or at least 7 diterpenic acids and/or diterpenic acid esters selected from the group consisting of: copalic acid, copaiferolic acid, agathendioic acid dimethyl ester, agathic acid, 3β-hydroxyanticopalic acid methyl ester, hardwickiic acid, 7α-acetoxyhardwickiic acid. Preferably it is the 7 diterpenic acids and/or diterpenic acid esters mentioned above.

TABLE 1

Molecular and structural formulas of the different diterpenic acids and/or diterpenic acid esters

| Name | Molecular formula | m/z | Structural formula |
|---|---|---|---|
| Copalic acid | C20H32O2 | 304 | |
| Copaiferolic acid | C20H32O3 | 320 | |
| Agathendioic acid dimethyl ester | C22H34O4 | 362 | |
| Agathic acid | C20H30O4 | 334 | |
| 3β-Hydroxyanticopalic acid methyl ester | C20H30O4 | 334 | |

TABLE 1-continued

Molecular and structural formulas of the different diterpenic acids and/or diterpenic acid esters

| Name | Molecular formula | m/z | Structural formula |
|---|---|---|---|
| Hardwickiic acid | C20H28O3 | 316 | |
| 7α-Acetoxyhardwickiic acid | C22H30O5 | 374 | 1a: R = H |

Preferably, the mixture of diterpenic acids and/or diterpenic acid esters includes all the following diterpenic acids and/or diterpenic acid esters: copalic acid, copaiferolic acid, agathendioic acid dimethyl ester, agathic acid, 3β-hydroxyanticopalic acid methyl ester, hardwickiic acid, 7α-acetoxyhardwickiic acid.

The *Copaifera* extract according to the invention consisting of an oleoresin comprises, in weight percentage based on the total weight of the extract, between 7.5 and 40 wt % of the 7 diterpenic acids and/or diterpenic acid esters mentioned above, preferentially between 10 and 30 wt %.

The *Copaiefera* extract according to the invention consisting of an enriched oleoresin comprises, in weight percentage based on the total weight of the extract, between 48 and 90 wt % of the 7 diterpenic acids and/or diterpenic acid esters mentioned above, preferentially between 60 and 85 wt %.

TABLE 2

| Name | Mass content in the oleoresin (%) | Mass content of diterpene fraction (%) |
|---|---|---|
| Copalic acid | 3 to 13 | 15 to 50 |
| Hardwickiic acid | 0.5 to 1.5 | 2 to 15 |
| Copaiferolic acid | 1 to 6 | 10 to 30 |
| Agathic acid and 3β-hydroxyanticopalic acid methyl ester | 1 to 6 | 8 to 30 |
| Agathendioic acid dimethyl ester | 1 to 6 | 10 to 30 |
| 7α-Acetoxyhardwickiic acid | 1 to 8 | 3 to 15 |

In a particular embodiment, the *Copaifera* extract according to the invention comprises or consists of the non-volatile fraction of *Copaifera* oleoresin.

In another embodiment, the *Copaifera* extract according to the invention comprises or consists of a mixture of diterpenic acids and/or diterpenic acid esters.

This "non-volatile" fraction of *Copaifera* oleoresin includes the mixture of diterpenic acids and/or diterpenic acid esters and can be obtained after total or partial removal, preferably total removal, of the essential oil, in particular by hydrodistillation. This non-volatile fraction comprises at least 80 wt % and preferably between 80 and 90 wt % diterpenic acids and/or diterpenic acid esters based on the total weight of said fraction. This represents an extract consisting of enriched oleoresin with maximum enrichment.

The mixture of diterpenic acids and/or diterpenic acid esters can also be obtained from a *Copaifera* oleoresin, or from the "non-volatile" fraction of *Copaifera* oleoresin; in particular by liquid-liquid extraction until obtaining a mixture having a concentration of diterpenic acids and/or diterpenic acid esters between 50 and 100 wt %, particularly between 60 and 100 wt %, more particularly between 80 and 100 wt % diterpenic acids and/or diterpenic acid esters based on the total weight of the liquid fraction obtained after extraction and removal of the extraction solvent. This liquid fraction obtained after extraction and removal of the solvent represents said mixture.

The present invention also relates to a dermatological or cosmetic composition comprising a *Copaifera* extract according to the invention and as described above, with at least one dermatologically or cosmetically acceptable excipient, for use in the treatment of alopecia and/or seborrhoea.

According to an embodiment, the invention relates to a dermatological or cosmetic composition comprising a *Copaifera* extract according to the invention and as described above, with at least one dermatologically or cosmetically acceptable excipient, for use in the treatment of alopecia, characterized in that the *Copaifera* extract is the only anti-alopecia active principle in said composition.

Preferably, the treatment of alopecia aims to slow hair loss.

According to an embodiment, the invention relates to a dermatological or cosmetic composition comprising a *Copaifera* extract according to the invention and as described above, with at least one dermatologically or cosmetically acceptable excipient, for use in the treatment of seborrhoea, characterized in that the *Copaifera* extract is the only anti-seborrhoea active principle in said composition. In particular, the seborrhoea relates to seborrhoea of the scalp and/or skin, and preferably seborrhoea of the scalp.

Preferably the amount of *Copaifera* extract is between 0.05 wt % and 10 wt % based on the total weight of the composition.

The invention also relates to a composition according to the present invention for use in the treatment of alopecia and/or seborrhoea, in a form suitable for topical administration. In an advantageous way, the *Copaifera* extract is the only anti-alopecia active principle in the composition for use in the treatment of alopecia. According to another advantageous embodiment, the *Copaifera* extract is the only anti-seborrhoea active principle in the composition for use in the treatment of seborrhoea.

The treatment or prevention of alopecia can be the slowing of hair loss.

The seborrhoea may be selected from seborrhoea of the skin and seborrhoea of the scalp.

Topical administration may be administration to the hair and/or scalp and/or skin.

The invention also relates to a Composition according to the present invention for use in the treatment of alopecia and/or seborrhoea, in a form suitable for oral administration. A composition according to the invention is characterized in that it comprises from 0.05 wt % to 10 wt % extract according to the invention, based on the total weight of the composition. In a particular embodiment, the *Copaifera* extract according to the invention is the only active principle for the treatment of alopecia in said composition. According to another particular embodiment, the *Copaifera* extract according to the invention is the only active principle for the treatment of seborrhoea in the composition.

The invention also relates to the use a *Copaifera* extract according to the invention for the treatment and/or prevention of seborrhoea and/or alopecia.

The invention also relates to an anti-seborrhoeic composition comprising a *Copaifera* extract according to the invention and as described above, with at least one dermatologically or cosmetically acceptable excipient. The preferred anti-seborrhoeic composition is a composition suitable for topical administration. Advantageously, the anti-seborrhoeic composition according to the invention contains only the *Copaifera* extract according to the invention as an anti-seborrhoeic active principle.

The invention also relates to an anti-alopecia composition comprising a *Copaifera* extract according to the invention and as described above, with at least one dermatologically or cosmetically acceptable excipient. The preferred anti-alopecia composition is a composition suitable for topical administration. Advantageously, the anti-alopecia composition according to the invention contains only the *Copaifera* extract according to the invention as an anti-alopecia active principle.

The composition according to the invention as described above is characterized in that the amount of *Copaifera* extract is between 0.05 wt % and 10 wt % based on the total weight of the composition. The amount of extract may be adapted according to the nature of the extract, i.e. according to whether it is crude oleoresin, enriched oleoresin or the mixture of diterpenic acids and/or diterpenic acid esters. This amount may be between 0.05 and 10 wt % based on the total weight of the composition, more particularly between 1 and 10 wt %, between 2 and 7.5 wt % or between 3 and 6 wt %, for example.

In a particular embodiment, the *Copaifera* extract in the composition according to the invention comprises or consists of the non-volatile fraction of *Copaifera* oleoresin.

In another embodiment, the present invention also relates to a cosmetic method, in particular a non-therapeutic method, for the treatment or prevention of a disorder selected from oily skin, shiny skin, oily hair, oily scalp, and preferably oily hair, oily scalp; comprising the topical application of an extract according to the invention or a composition according to the invention. According to a particular embodiment, the cosmetic, in particular non-therapeutic, method is characterized in that the *Copaifera* extract according to the invention is the only active principle intended for the treatment or prevention of a disorder selected from oily skin, shiny skin, oily hair, oily scalp and preferably oily hair, oily scalp.

In another embodiment, the present invention also relates to a cosmetic, in particular non-therapeutic, method for mattifying seborrhoeic skin.

The extract according to the invention may be combined or mixed with a lipid carrier or vehicle in order to standardize the content of diterpenic acids and/or diterpenic acid esters in the composition according to the invention.

The lipid carrier or vehicle may be an oil, in particular a dermatologically or cosmetically acceptable oil.

In the present invention, "dermatologically or cosmetically acceptable" means that which is useful in the preparation of a dermatological or cosmetic composition, which is generally safe, non-toxic and neither biologically nor otherwise undesirable and which is acceptable for dermatological or cosmetic use, in particular by topical application.

The compositions according to the invention are advantageously intended for topical application, especially on the skin.

The compositions according to the invention may thus be in the forms that are usually known for topical administration, i.e. lotions, foams, gels, dispersions, emulsions, sprays, serums, masks or creams, with excipients allowing in particular skin penetration in order to improve the properties and accessibility of the active principle.

Advantageously, it will be a cream.

These compositions generally contain, in addition to the extract according to the present invention, a physiologically acceptable medium, usually based on water or solvent, for example alcohols, ethers or glycols. They may also contain surfactants, complexing agents, preservatives, stabilizers, emulsifiers, thickeners, gelling agents, humectants, emollients, trace elements, essential oils, perfumes, dyes, mattifying agents, chemical or mineral filters, moisturizing agents, geothermal waters, etc.

These compositions may further contain other active principles leading to a complementary or possibly synergistic effect.

Pharmacological Evaluation

The following example illustrates the invention without limiting its scope.

Example 1: Effects of Different Compounds on the 5α-Reductase Activity of Fibroblasts Derived from Human Follicle Dermal Papillae The objective of this study was to evaluate the potential inhibitory activity of different compounds on 5α-reductase.

Materials and Methods

The study is performed on human cells derived from donor follicle dermal papillae. This model is attractive since dermal papillae have the 5α2 isoform as in prostate tissue. The cells are seeded in 24-well plates and cultured for 24 hours in DMEM culture medium supplemented with L-glutamine (2 mM), penicillin (50 U/ml), streptomycin (50 µg/ml) and fatal calf serum (10%) under standard culture conditions (37° C. and 5% $CO_2$). The culture medium is then replaced by a DMEM analytical medium supplemented with L-glutamine (2 mM), penicillin (50 U/ml), streptomycin (50 µg/ml) and fatal calf serum (1%). This analytical medium may contain or may not contain (control conditions) the products to be tested and a compound used as reference, finasteride (10 µM), for 24 h of pre-incubation. The cells were then treated with an analytical medium containing [$C^{14}$]-testosterone and containing or not containing (control conditions) the test or reference products, and the cells were incubated for 24 h under these conditions. After incubation, supernatants were collected for testosterone metabolism analysis. All experiments were carried out three times. The steroid molecules were extracted from the supernatants with a chloroform/methanol mixture. The organic phase was collected and the different molecular species (testosterone metabolites) were separated by thin-layer chromatography using a solvent system containing dichloromethane, ethylacetate and methanol. An autoradiography was performed on the chromatography and the transformed testosterone was estimated by densitometric analysis.

Thus, the metabolism of testosterone to dihydrotestosterone reflects the 5α-reductase activity and is evaluated by the dihydrotestosterone/testosterone ratio.

Results

A first group of experiments highlights the effects of *Copaifera officinalis* oleoresin (Table 3 below). Surprisingly, the inventors have demonstrated a significant and reproducible activity of 5α-reductase inhibition by *Copaifera officinalis* oleoresin, this inhibition even appears concentration-dependent. The strong inhibition of this enzyme by finasteride indeed validates all these experiments.

TABLE 3

Effects of *Copaifera officinalis* oleoresin and finasteride on testosterone metabolism/dihydrotestosterone production (5α-reductase activity; n = 3)

|  | Finasteride | Oleoresin (*C. officinalis*) | |
|---|---|---|---|
| Control | 10 µM | 10 µg/ml | 30 µg/ml |
| 100 | −77% | −15% | −27% |
|  | ** p < 0.01 | * p < 0.05 | ** p < 0.01 |

The statistical study is carried out versus the control group (Dunnett's test).

The oleoresin tested was prepared according to the method described in Example A.

By way of comparison, a *Serenoa repens* extract, a *Curcubita pepo* extract as well as the compound glyceryl laurate were also tested in one of these experiments.

At 10 µg/ml, the *Serenoa repens* extract does not induce significant inhibition of 5α-reductase. At 20 µg/ml, however, this extract induces a 23% inhibition reaching statistical significance (p<0.05 versus control).

A significant inhibition of 17% is obtained for a *Curcubita pepo* extract tested at 100 µg/ml.

A significant inhibition of 19% is obtained for glyceryl laurate tested at 40 µg/ml.

A second series of experiments was conducted to evaluate whether the inhibitory activity on 5α-reductase was carried by the non-volatile fraction or rather by the volatile fraction corresponding to the essential oil. The results are summarized in Table 4 below. The preparation of the volatile and non-volatile fractions is carried out according to the method described in Example C with the diethyl ester as apolar solvent.

TABLE 4

Effects of non-volatile and volatile fractions from *Copaifera officinalis* oleoresin on testosterone metabolism/ dihydrotestosterone production (5α-reductase activity)

|  | Non-volatile fraction | | | Volatile fraction | |
|---|---|---|---|---|---|
| Control | 0.3 µg/ml | 1 µg/ml | 3 µg/ml | 7.7 µg/ml | 23.1 µg/ml |
| 100 | 0 | −6% | −14% | +2% | +9% |
|  | p = NS | p = NS | * p < 0.05 | p = NS | p = NS |

The statistical study is carried out versus the control group (Dunnett's test).

It turns out that the activity of *Copaifera officinalis* oleoresin is carried by the non-volatile fraction, indeed no activity of the volatile fraction was detected. Inhibition of 5α-reductase is only 14% at 3 µg/mL (10× less concentrated than the oleoresin), but this reduction reaches statistical significance (p<0.05).

A third series of experiments was carried out to show that other *Copaifera* species, in particular *C. multijuga*, also had an advantageous activity on 5α-reductase inhibition. The inventors focused on the non-volatile fraction, which carries the inhibitory activity. The results are summarized in Table 3 below.

TABLE 5

Effects of non-volatile fractions from the resin of *Copaifera multijuga* on testosterone metabolism/dihydro-testosterone production (5α-reductase activity; n = 2)

|  | Non-volatile fraction *Copaifera multijuga* | |
|---|---|---|
| Control | 1 µg/ml | 10 µg/ml |
| 100 | 0<br>p = NS | −31%<br>** p < 0.01 |

The statistical study is carried out versus the control group (Dunnett's test).

The preparation of the volatile and non-volatile fractions is carried out according to the method described in Example C with the diethyl ester as apolar solvent.

These results clearly show that several *Copaifera* species are of interest. Indeed, the non-volatile fraction of the species *C. multijuga* reaches 31% inhibition of 5α-reductase at 10 µg/ml.

All these results lead to the conclusion that *Copaifera* oleoresin has an extremely advantageous inhibitory activity on 5α-reductase. This activity is carried by the non-volatile fraction of the resin. Finally, the inventors have also shown that this activity is found on several *Copaifera* species.

EXAMPLES

Preparation of Oleoresin

Example A

The trunk bark of *Copaifera officinalis* and/or *Copaifera multijuga* and/or *Copaifera reticulata* trees is notched to recover the oleoresin. This is then homogenized and stabilized under nitrogen.

The active substance is 100% raw oleoresin from the trunk of *Copaifera officinalis* and/or *Copaifera officinalis* and/or *Copaifera. multijuga* and/or *Copaifera. Reticulata*.

LCMS Analysis of a *Copaifera officinalis* Oleoresin:

Each sample was analysed by UHPLC-QTOFMS using a conventional linear gradient. Separation on a Waters Acquity UHPLC system.

Column 100×2.1 mm, 1.7 µm, Acquity BEH C18 equipped with a pre-column
Mobile phase:
Mobile phase A: LCMS grade water +0.1% formic acid
Mobile phase B: LCMS grade acetonitrile+0.1% formic acid Gradient

| Time (min) | % A | % B |
|---|---|---|
| 0-0.5 | 50 | 50 |
| 0.5-4 | 50 → 40 | 50 → 60 |
| 4-12 | 40 → 1 | 60 → 99 |
| 12-15 | 1 | 99 |
| 15-15.5 | 1 → 50 | 99 → 50 |
| 15.5-19 | 50 | 50 |

Acquisitions: UV 220 nm

| Structure | m/z | Content in the oleoresin (weight % relative to the weight of oleoresin) |
|---|---|---|
| Copalic acid | 304 | 5.69 |
| Hardwickiic acid | 316 | 0.61 |
| Copaiferolic acid | 320 | 2.90 |
| Agathic acid and 3β-hydroxyanticopalic acid methyl ester | 334 | 2.35 |
| Agathendioic acid dimethyl ester | 362 | 2.92 |
| 7α-Acetoxyhardwickiic acid | 374 | 0.79 |

Preparation of Non-Volatile Fraction

Example B

The oleoresin obtained according to the preceding Example A is suspended in 10 volumes of water heated to 100° C. for 4 h to make a hydrodistillation. The volatile essential oil is recovered by condensation. After hydrodistillation, the distillation residue is recovered. After drying by lyophilization or other drying means, the residue constitutes the non-volatile fraction.

Example C 1 volume of *Copaifera* oleoresin obtained according to the preceding Example A is diluted in 8 to 10 volumes of a water-immiscible lipophilic solvent (such as diethyl ether, ethyl acetate). This solution is extracted by liquid/liquid extraction with a 5% sodium hydroxide (NaOH) solution. The operation is repeated 3 times with 4 to 5 V of 5% NaOH. The lower phase (basic aqueous phase) is acidified by the addition of 1 N hydrochloric acid (HCl) and then extracted by liquid/liquid extraction with a water-immiscible apolar solvent (such as diethyl ether, ethyl acetate). The ethyl acetate phase is washed with water and then dried over $Na_2SO_4$. After removal of the solvent by rotavapor or other drying means, the dry residue obtained corresponds to the mixture of diterpenic acids and/or diterpenic acid esters according to the invention.

| Structure | m/z | Weight content in the non-volatile fraction |
|---|---|---|
| Copalic acid | 304 | 28.45 |
| Hardwickiic acid | 316 | 3.05 |
| Copaiferolic acid | 320 | 14.52 |
| Agathic acid | 334 | 11.77 |

-continued

| Structure | m/z | Weight content in the non-volatile fraction |
|---|---|---|
| and 3β-hydroxyanticopalic acid methyl ester | | |
| Agathendioic acid dimethyl ester | 362 | 14.58 |
| 7α-Acetoxyhardwickiic acid | 374 | 3.96 |

Example: Anti-Hair Loss Hair Composition

*Copaifera officinalis* oleoresin according to Example A from 0.05 to 10%.
DEXPANTHENOL from 0.3 to 1%
ISOPROPYL ALCOHOL from 1 to 5%.
PPG-26-BUT.-26/PEG-40 from 2 to 10%.
ETHYL ALCOHOL from 10 to 40%.
FRAGRANCE from 0.2 to 1%
WATER q.s.

Example: Anti-Seborrhoea Composition

Non-volatile fraction according to Example B: from 0.05 to 10%.
Glycerine: from 2% to 5%.
Phenoxyethanol: from 0.3 to 0.5%.
Na2EDTA: from 0.1 to 0.2%.
Polyacrylate-13 and Polyisobutene and Polysorbate 20 & water: from 1% to 2%.
Glyceryl stearate and PEG-100 stearate: from 2 to 5%.
Cyclopentasiloxane: from 3% to 5%.
Cetyl alcohol: from 1% to 2%.
Glycerol tri-2-ethylhexanoate: from 2% to 3%.
Dicapryl carbonate: from 2% to 3%.
Polymethylacrylate: from 2% to 3%.
Fragrance: from 0.1% to 1%.
Water q.s.

The invention claimed is:

1. A method for the treatment of seborrhoea and/or alopecia in a human in need thereof consisting essentially of administering to the skin or scalp of the human in need thereof a therapeutically effective amount of a non-volatile fraction of *Copaifera* oleoresin to effectively treat the seborrhoea and/or alopecia in the human in need thereof; wherein the non-volatile fraction of *Copaifera* oleoresin is obtained from *Copaifera officinalis, Copaifera* multijugla, and/or *Copaifera* reticulate by using hydrodistillation on an *Copaifera* oleoresin and then lyophilizing it to yield the non-volatile fraction of *Copaifera* oleoresin which is used to effectively treat the seborrhoea and/or alopecia in the human in need thereof.

2. The method according to claim 1, wherein the non-volatile fraction of *Copaifera* oleoresin is between 7.5% and 95 wt % diterpenic acids and/or diterpenic acid esters.

3. The method according to claim 1, wherein the non-volatile fraction of *Copaifera* oleoresin is at least 7.5 wt % of a mixture of diterpenic acids and/or diterpenic acid esters based on the total weight of the non-volatile fraction of *Copaifera* oleoresin.

4. The method according to claim 1, wherein the non-volatile fraction of *Copaifera* oleoresin is enriched in a mixture of diterpenic acids and/or diterpenic acid esters containing, in weight percentage, between 48% and 90 wt % diterpenic acids and/or diterpenic acid estersbased on the total weight of the enriched *Copaifera* oleoresin.

5. The method according to claim 1, wherein the non-volatile fraction of *Copaifera* oleoresin is a non-volatile fraction of *Copaifera* oleoresin.

6. The method according to claim 1, wherein the non-volatile fraction of *Copaifera* oleoresin is a mixture of diterpenic acids and/or diterpenic acid esters.

7. The method according to claim 1, wherein the non-volatile fraction of *Copaifera* oleoresin is a mixture of diterpenic acids and/or diterpenic acid esters comprising at least 2, or at least 3, or at least 4, or at least 5, or at least 6, or at least 7 diterpenic acids and/or diterpenic acid esters selected from copalic acid, copaiferolic acid, agathendioic acid dimethyl ester, agathic acid, 3β-hydroxyanticopalic acid methyl ester, hardwickiic acid, and 7α-acetoxyhardwickiic acid.

8. The method according to claim 1, wherein the non-volatile fraction of *Copaifera* oleoresin is a mixture of diterpenic acids and/or diterpenic acid esters comprising the following diterpenic acids and/or diterpenic acid esters: copalic acid, copaiferolic acid, agathendioic acid dimethyl ester, agathic acid, 3β-hydroxyanticopalic acid methyl ester, hardwickiic acid, 7α-acetoxyhardwickiic acid.

9. The method according to claim 1, wherein is the non-volatile fraction of *Copaifera* oleoresin is formulated into a dermatological or cosmetic composition with at least one dermatologically or cosmetically acceptable excipient, and wherein the dermatological condition is alopecia.

10. The method according to claim 1, wherein the non-volatile fraction of *Copaifera* oleoresin is the only anti-alopecia active principle in the method.

11. The method according to claim 1, wherein is the non-volatile fraction of *Copaifera* oleoresin is formulated as a dermatological or cosmetic composition with at least one dermatologically or cosmetically acceptable excipient, and wherein the dermatological condition is seborrhoea.

12. The method according to claim 1, wherein the non-volatile fraction of *Copaifera* oleoresin is the only anti-seborrhoea active principle in said method.

13. The method according to claim 1, wherein the amount of non-volatile fraction of *Copaifera* oleoresin is between 0.05 wt % and 10 wt % based on the total weight of the method.

14. The method according to claim 1, wherein the seborrhoea is seborrhoea of the scalp and/or skin, and preferably seborrhoea of the scalp.

15. The method according to claim 1, wherein the composition, in a form suitable for topical administration.

16. The method according to claim 1, wherein the non-volatile fraction of *Copaifera* oleoresin which is at least 15 wt %, or at least 20 wt %, or at least 25 wt % of a mixture of diterpenic acids and/or diterpenic acid esters based on the total weight of the non-volatile fraction of *Copaifera* oleoresin.

17. The method according to claim 1, wherein the non-volatile fraction of *Copaifera* oleoresin is enriched in a mixture of diterpenic acids and/or diterpenic acid esters containing, in weight percentage, between 50% and 90 wt %, or between 60% and 90 wt % or between 70% and 90 wt %, or between 80% and 90 wt % diterpenic acids and/or diterpenic acid esters based on the total weight of the enriched *Copaifera* oleoresin.

\* \* \* \* \*